United States Patent
Walters et al.

(10) Patent No.: US 6,221,053 B1
(45) Date of Patent: *Apr. 24, 2001

(54) MULTI-FEATURED MEDICATION DELIVERY PEN

(75) Inventors: Daniel A. Walters, Rockaway Township, NJ (US); Christopher J. Brooks, Glen Head, NY (US); Diego Y. Fontayne, Teaneck, NJ (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,938

(22) Filed: Feb. 20, 1998

(51) Int. Cl.[7] ..................................................... A61M 5/00
(52) U.S. Cl. .............................................. 604/211; 604/208
(58) Field of Search .................................. 604/207, 208, 604/209–211, 218

(56) References Cited

U.S. PATENT DOCUMENTS

| | | | |
|---|---|---|---|
| 5,279,585 | * | 1/1994 | Balkwill ............................... 604/207 |
| 5,292,318 | * | 3/1994 | Haber et al. ......................... 604/207 |
| 5,304,152 | * | 4/1994 | Sams ..................................... 604/208 |
| 5,674,204 | * | 10/1997 | Cvhanoch ............................ 604/207 |
| 5,679,111 | * | 10/1997 | Hjertman et al. .................... 604/208 |
| 5,725,508 | * | 3/1998 | Chanoch et al. .................... 604/211 |
| 5,728,074 | * | 3/1998 | Castellano et al. ................. 604/211 |
| 5,743,889 | * | 4/1998 | Sams ..................................... 604/218 |

* cited by examiner

Primary Examiner—Sharon Kennedy
(74) Attorney, Agent, or Firm—Alan W. Fiedler, Esq.

(57) ABSTRACT

A medication delivery pen having a repeat-dose feature that limits motion of the dose control mechanism using an adjustable repeat-dose stop on the dose knob. In addition, the medication delivery pen also provides the user a simple mechanism for setting and correcting the dose and a drive mechanism that makes the dispensing operation as easy as possible requiring as little force as necessary.

8 Claims, 5 Drawing Sheets

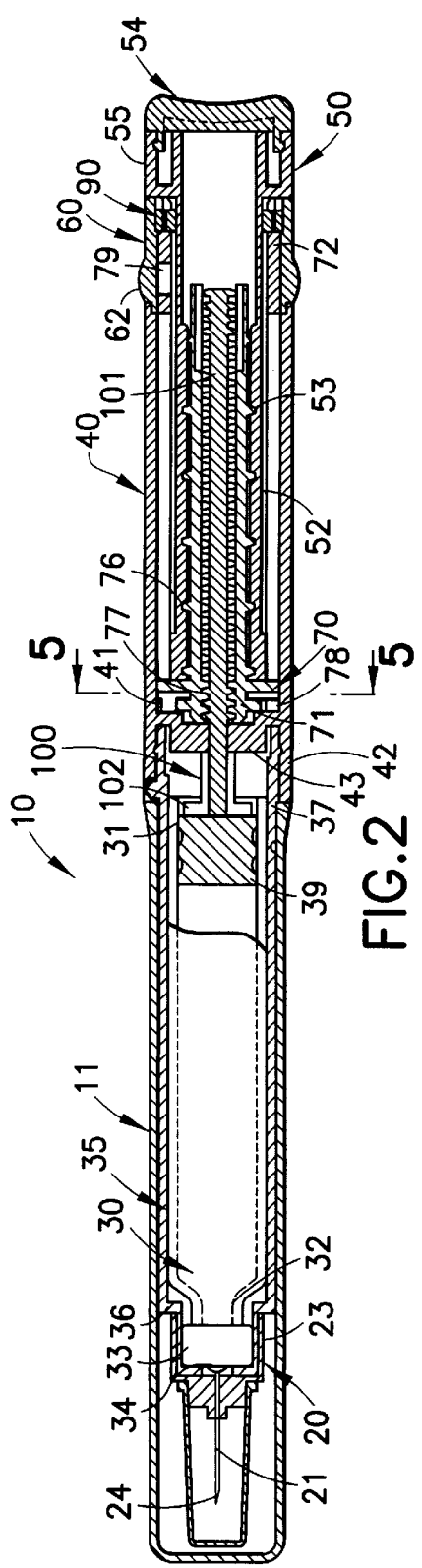
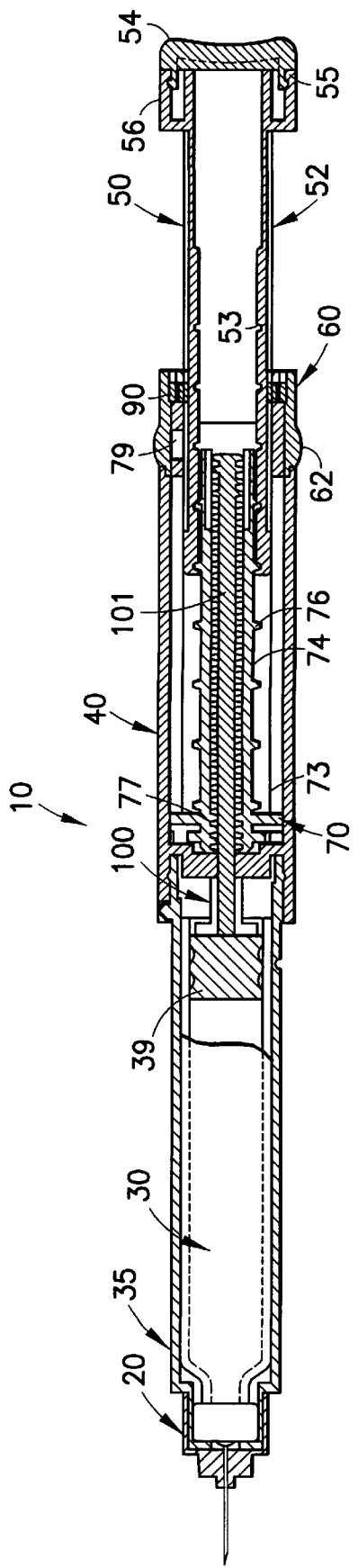

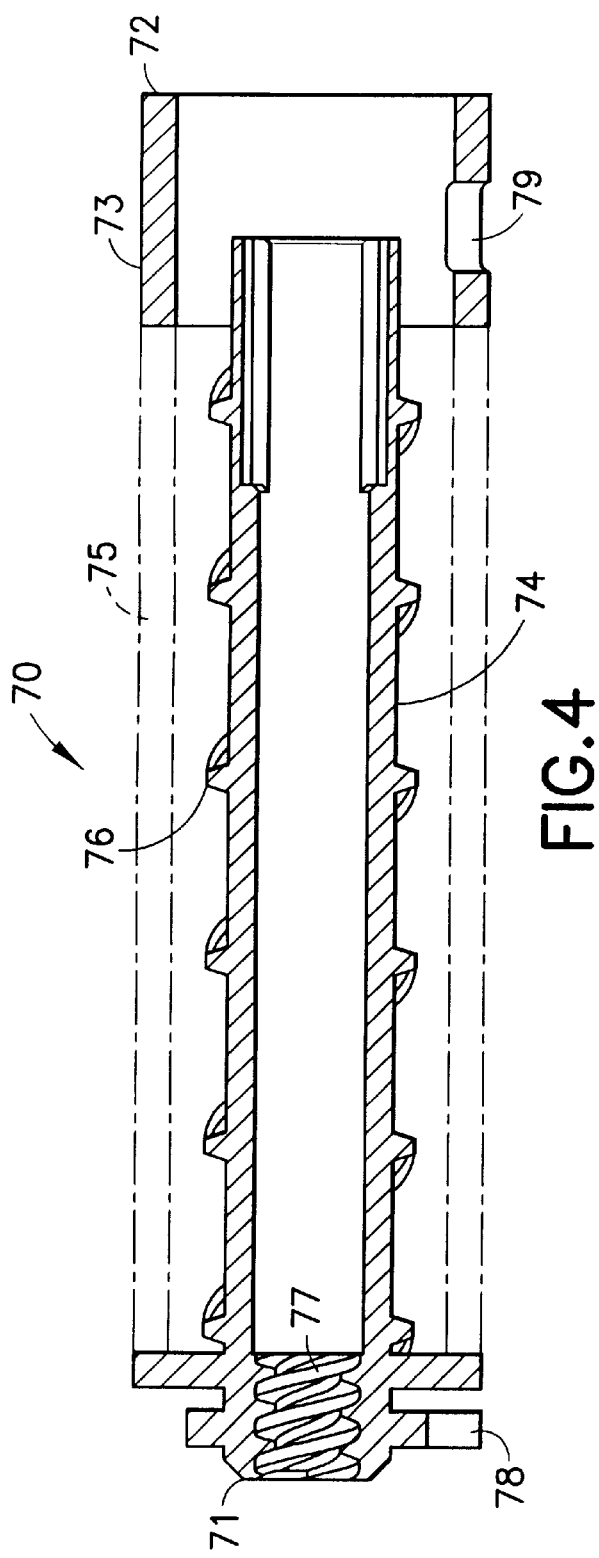
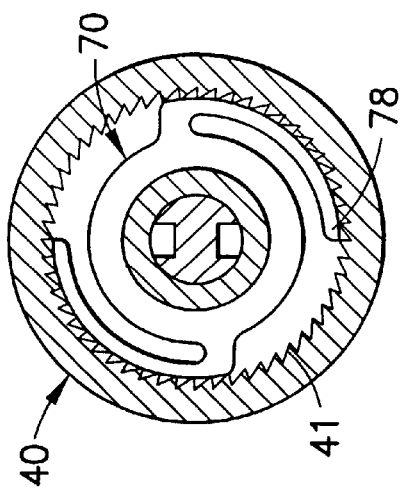
FIG. 4
FIG. 5

MULTI-FEATURED MEDICATION DELIVERY PEN

BACKGROUND OF THE INVENTION

1. Field of the Invention

The present invention relates to a medication delivery pen having a variety of features and, more particularly, a medication delivery pen that provides a mechanical advantage that uses less force to delivery the selected dose than would be needed to push directly on a plunger within a vial, a re-settable and/or repeatable dosing feature, and a self-priming feature all within the device using relatively few components.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described medication delivery pen is effective and much more convenient for self-administration of medication than the hypodermic syringes that use separate medication vials. However, the above-described medication delivery pens require the user to continually set or reset the desired dose before each injection. As a result, users with impaired vision and fine motor skills have found it difficult to readily set the dose on such pens especially when using a medication delivery pen having a wide range of dosage settings available. Since it is particularly common among patients with diabetes to have complications of the disease causing impaired vision and fine motor skills even more of a need has been found to address this problem. Hence, it is necessary to provide a medication delivery pen having a simple mechanism for setting the desired dose, repeating the dose when necessary, and priming the medication delivery pen prior to use. It is also important to provide a medication delivery pen that makes the dispensing operation as easy as possible requiring as little force as necessary.

SUMMARY OF THE INVENTION

The present invention relates to a medication delivery pen that addresses the aboveidentified problems. The medication delivery pen has a repeat-dose feature that limits motion of the dose control mechanism using an adjustable repeat-dose stop on the dose knob. In addition, the medication delivery pen also provides the user a simple mechanism for setting and correcting the dose and a drive mechanism that makes the dispensing operation as easy as possible requiring as little force as necessary.

Another feature of the present invention is that the medication delivery pen provides a simple means for retracting the plunger when reloading the medication delivery pen with a new vial.

BRIEF DESCRIPTION OF THE DRAWINGS

FIG. 2 is a cross-sectional view of the medication delivery pen shown in FIG. 1 fully assembled and in a ready for use condition.

FIG. 3 is a cross-sectional view of the medication delivery pen shown in FIG. 2 in a set dose condition and ready for dispense of medication.

FIG. 4 is a cross-sectional view of the rod barrel tube shown in FIG. 1.

FIG. 5 is a cross-sectional view of the medication delivery pen shown in FIG. 2 along line A—A.

DETAILED DESCRIPTION OF THE INVENTION

Figure 1:
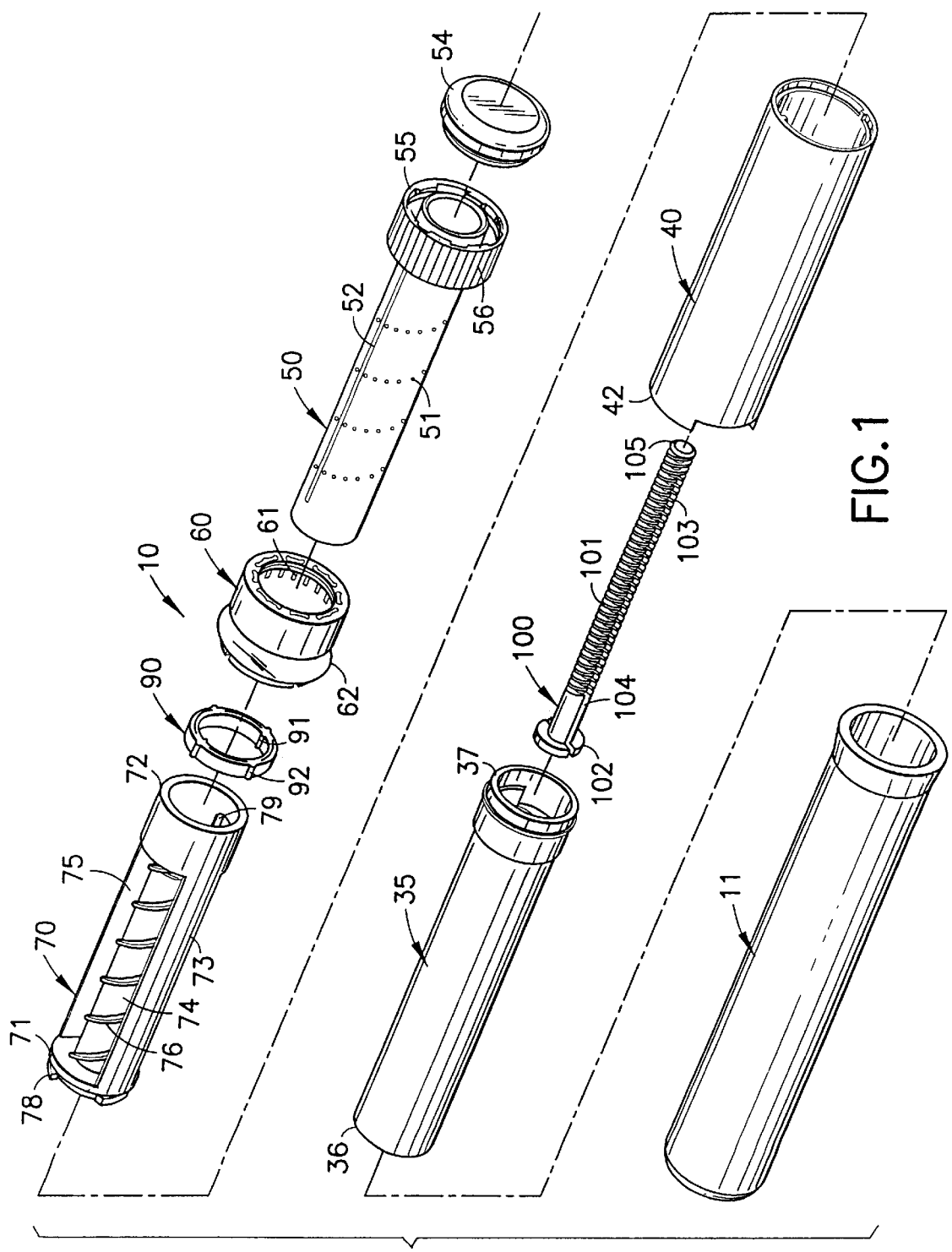
FIG. 1 is an exploded perspective view of a medication delivery pen according to the present invention.

A multi-feature medication delivery pen 10 according to the present invention is shown in FIG. 1. Medication delivery pen 10 includes a cap 11 removably attached to a body 40 so to cover a vial retainer 35 containing a vial 30. As shown in FIG. 2 vial 30 includes a proximal end 31 and a distal end 32 having a vial cap 33 that securely holds a vial septum 34 on distal end 32. Vial 30 also includes a vial piston 39 therein to form a sterile sliding seal within vial 30 to hold medication therein. As shown in FIG. 2 a pen-needle assembly 20 is releasably engaged to a distal end 36 of vial retainer 35. Pen-needle assembly 20 includes a double-ended needle cannula 21 having a distal point 24 and a proximal point (not shown). Double-ended needle cannula 21 is mounted on a hub 23 including means for attaching hub 23 to distal end 36 of vial retainer 35. A proximal end 37 of vial retainer 35 is snap-fit onto a distal end 42 of body 40 or can be mounted thereto by other means, e.g., threads.

As shown in FIGS. 1–3, medication delivery pen 10 includes a rod barrel tube 70, a clicker 90, a lens and ring assembly 60, and a dose knob 50. Rod barrel tube 70 includes a distal end 71 and a proximal end 72, with an outer barrel 73 extending from distal end 71 and surround a rod barrel 74. As shown in FIG. 1 outer barrel 73 may have a pair of openings 75 through its outer surface. Rod barrel 74 includes a set of external threads 76 that mate with a set of internal threads 53 within dose knob 50, described below, and a set of internal threads 77 that mate with a threaded shaft 101 on a plunger 100 having a distal face 102 and a proximal end 105. Plunger 100 also includes a pair of keyways 104 extending from distal face 102 to a keyway stop 103 near proximal end 105. Rod barrel tube 70 also include a plurality of ratchet pawls 78 at distal end 71 that are received within body 40 and engage with ratchet 41 located within body 40 near its distal end 42. Distal end 42 of body 40 also includes a pair of keys 43, shown in FIG. 2, that extend into body 40 to engage with the pair of keyways 104 on plunger shaft 101 of plunger screw 100. Rod barrel tube 70 also includes a window 79 located near its proximal end 72 through which a plurality of dosage numerals 51 printed on dose knob 50 are visible to a user for setting of the desired dose. Dose knob 50 also includes a dose knob cap 54 that is permanently attached to a proximal end 55 of dose knob 50. Dose knob 50 also includes internal threads 53 that engage rod barrel outer diameter threads 76 on rod barrel 74 so that dose knob 50 is threaded out of rod barrel tube 70 as a dose is being set, as shown in FIG. 3. During the dose setting operation rod barrel tube 70 is prevented from rotating within body 40 by interaction of ratchet pawl 78 on rod barrel tube 70 and ratchet 41 within body 40.

Dose knob 50 also includes a plurality of key slots 52 arranged axially on the outer surface of dose knob 50 so to receive a matched plurality of keys 91 on the inside of clicker 90 as clicker 90 is mounted onto dose knob 50. Clicker 90 also includes a plurality of clicker fingers 92 on its outer circumference that interacts with a plurality of slots 61 within lens and ring assembly 60. Interaction between clicker fingers 92 and slots 61 occur during the dose setting operation to provide the user with audible and/or tactile feedback during this operation. Lens and ring assembly 60 provide a feature of magnifying the dosage numeral 51 on the outside surface of dose knob 50 to aide the user in setting the dose during the setting operation using lens 62 integrated thereto.

Dose knob 50 has an enlarged proximal end 55 onto which dose knob cap 54 has been attached and may have a textured surface and/or an indentation to provide easy operator manipulation of dose knob 50 during dose setting of medication delivery pen 10. In addition, it should be appreciated that dose knob cap 54 could be integrally molded at proximal end 55 of dose knob 50.

FIG. 5 is a cross-sectional view of medication delivery pen 10 shown in FIG. 2 along lines A—A and more clearly show the interaction between the ratchet 41 within body 40 and ratchet pawl 78 at distal end 71 of rod barrel tube 70. FIG. 5 also shows that ratchet pawl 78 at ratchet surface 41 only prevent rotation in one direction so that after a dose has been set as shown in FIG. 3 and pressure is applied to dose knob cap 54 rod barrel tube 70 is free to rotate within body 40. As rod barrel tube 70, rotates interaction between rod barrel internal threads 77 and threaded shaft 101 of plunger screw 100 occurs to move plunger screw 100 in the distal direction a distance corresponding to the desired dose that was set. Plunger screw 100 moves in the distal direction because it is prevented from rotation by interaction of keys 43 in body 40 and keyways 104 on plunger screw 100.

Figure 6:
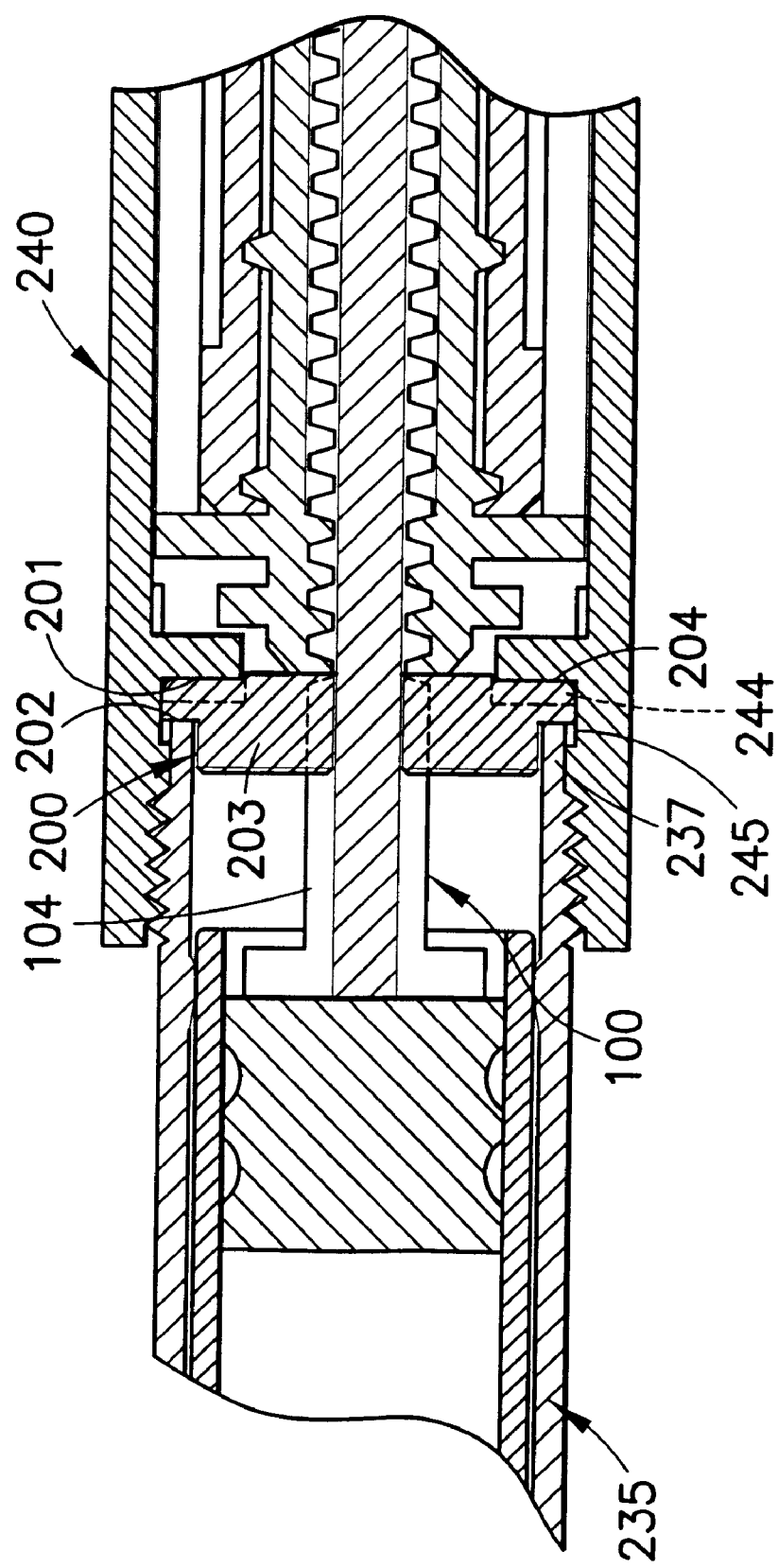
FIG. 6 is a cross-sectional view of a portion of an alternative medication delivery pen that has a feature that it allows it to be reloadable.

FIG. 6 is a cross-sectional view of a section of an alternative medication delivery pen that provides the pen with the ability to be reloaded when vial has been fully used and must be replaced. This embodiment is substantially similar to the earlier embodiment except that key 43 within body 40 has been replaced with a plunger screw key 200 that is free to rotate when vial retainer 235 is removed from body 240, but when vial retainer 235 is fully threaded to pen body 240 plunger screw key 200 is prevented from rotating. Plunger screw key 200 includes a proximal face 201 having a plurality of teeth that engage with matching plurality of teeth 244 within body 240. Plunger screw key 200 also includes a shoulder 202 around the circumference that is received in a circumferencial internal diameter clearance slot 245 within body 240 to retain plunger screw key 200 within body 240. Plunger screw 200 also includes a pair of keys 203 that engage keyway 104 and plunger screw 100, discussed above. Interaction between key 203 and keyway 104 prevent plunger screw 100 from rotating when plunger screw key 200 is prevented from rotating because of the interaction between key 204 on plunger screw key 200 and key 244 within body 240 when a proximal end 237 of vial retainer 235 applies sufficient pressure on shoulder 202.

Figure 7:
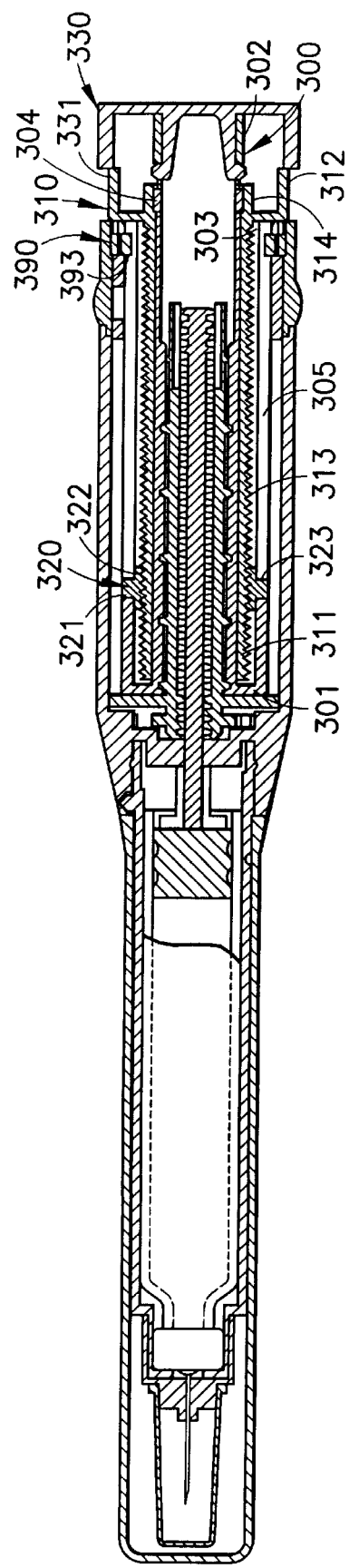
FIG. 7 is a cross-sectional view of yet another medication delivery according to the present invention having means for setting a desired dose and repeating delivery of that desired dose in consecutive injections.

FIG. 7 is yet another embodiment of a medication delivery pen according to the present invention and, more particularly, shows a feature that allows the user to set a desired dose for repeated delivery. As shown in FIG. 7 this feature is provided by the incorporation into the first embodiment of a dose knob having a distal end 301 and a proximal end 302, wherein proximal end 302 includes a well about its outer surface and a plurality of stop adjuster rotation detents 304 are located within proximal end 302 of dose knob 300. A stop adjuster 310 includes a distal end 311 and a proximal end 312 with distal end 311 being inserted into circumferencial well 303 in dose knob 300. Stop adjuster 310 also includes a set of external threads 313 and a plurality of stop adjuster rotational detents 314 within an inner surface that engage with corresponding stop adjuster rotational detents 304 on dose knob 300. Stop adjuster rotation detents 304 and 314 provide the user with tactile feedback during the operation of setting the repeat dose.

A dose stop 320 includes a plurality of dose stop keys 321 extending radially from dose stop 320 and a set of internal threads 322 that engage with outer threads 313 on stop adjuster 310. A dose knob cap 330 is attached to dose knob 300 after stop adjuster 310 has been mounted on dose knob 300 to retain stop adjuster 310 thereon. In addition, dose knob cap 330 can provide a textured surface and/or indentations for use during dose setting, as described above.

After a dose has been set by the user, the user would rotate stop adjuster 310 to move dose stop 320 in a proximal direction until a proximal face 323 of dose stop 320 comes into contact with a distal face 393 on a clicker 390. Of course, clicker 390 provides the same features and functions as clicker 90 in the earlier embodiment. Rotation of stop adjuster 310 cause dose stop 320 to move because of interaction between internal threads 322 and stop adjuster outer diameter thread 313 and interaction between dose stop key 321 and a dose knob keyway 305 on dose knob 300. When dose stop is in the position desired by the user further proximal movement of the dose knob is prevented beyond the set desired dose. Dose stop 320 remains in the position it has been set to until change at a later point by the user via stop adjuster 310.

While the present invention has been described with respect to a preferred and a number of alternative embodiments, it is apparent that various changes can be made without departing from the scope of the invention as defined by the appended claims.

What is claimed is:

1. A medication delivery pen comprising:
   a pen-needle having a cannula mounted on a hub;
   a vial retainer including a vial containing a medication to be delivered and having said pen-needle removably attached to a distal end; and
   a housing having said vial retainer mounted to a distal end and including;
      a body;
      a dose control mechanism for setting a desired dose to be delivered from the vial;
      a drive mechanism for dispensing the desired dose from the vial;
      a rod barrel tube within said body for interfacing said dose control mechanism with said drive mechanism; and
      a radial ratchet mechanism interfacing said housing and said rod barrel tube to prevent rotation of said rod barrel tube and said drive mechanism with respect to said housing when said dose control mechanism is being used to set the desired dose.

2. A medication delivery pen according to claim 1, wherein said rod barrel tube includes an outer thread for engaging said dose control mechanism and an inner thread for engaging said drive mechanism.

3. A medication delivery pen according to claim 1, further comprising a means on said rod barrel tube for displaying the dose set by said dose control mechanism.

4. A medication delivery pen according to claim 3, wherein said means for displaying the dose includes a window within said rod barrel tube.

5. A medication delivery pen according to claim 1, further comprising means within said housing for resetting said drive mechanism when a new vial is loaded into said vial retainer.

6. A medication delivery pen according to claim 1, further comprising means for repeating the desired dose.

7. A medication delivery pen according to claim 6, wherein said means for repeating the desired dose includes an adjustable repeat dose stop in said dose control mechanism that limits axial motion of said dose control mechanism when setting the desired dose.

8. A medication delivery pen according to claim 7,
   wherein said dose control mechanism includes a dose knob, and
   wherein said adjustable repeat dose stop is mounted in said dose knob to limit motion of said dose knob when repeating the desired dose.

* * * * *